United States Patent
Kaye

(10) Patent No.: US 9,710,754 B2
(45) Date of Patent: Jul. 18, 2017

(54) INFERENCE ELECTRONIC SHELF LIFE DATING SYSTEM FOR PERISHABLES

(71) Applicant: INFRATAB, INC., Oxnard, CA (US)

(72) Inventor: Stanton Kaye, Oxnard, CA (US)

(73) Assignee: INFRATAB, INC., Oxnard, CA (US)

( * ) Notice: Subject to any disclaimer, the term of this patent is extended or adjusted under 35 U.S.C. 154(b) by 3 days.

(21) Appl. No.: 14/681,860

(22) Filed: Apr. 8, 2015

(65) Prior Publication Data

US 2016/0012337 A1    Jan. 14, 2016

Related U.S. Application Data

(63) Continuation of application No. PCT/US2013/064177, filed on Oct. 9, 2013.

(60) Provisional application No. 61/711,340, filed on Oct. 9, 2012.

(51) Int. Cl.
  *G06N 5/04* (2006.01)
  *G06N 99/00* (2010.01)
  *G06Q 10/08* (2012.01)

(52) U.S. Cl.
  CPC ............ *G06N 5/04* (2013.01); *G06N 99/005* (2013.01); *G06Q 10/08* (2013.01); *G06Q 10/0833* (2013.01)

(58) Field of Classification Search
  CPC ................................ G06N 99/00; G06N 5/04
  USPC ........................................................ 706/12
  See application file for complete search history.

(56) References Cited

U.S. PATENT DOCUMENTS

| | | |
|---|---|---|
| 3,967,579 A | 7/1976 | Seiter |
| 4,057,029 A | 11/1977 | Seiter |
| 4,061,033 A | 12/1977 | Nixon |
| 4,277,974 A | 7/1981 | Karr et al. |
| 4,384,288 A | 5/1983 | Walton |
| 4,388,524 A | 6/1983 | Walton |
| 4,546,241 A | 10/1985 | Walton |
| 4,580,041 A | 4/1986 | Walton |
| 4,746,823 A | 5/1988 | Lee |
| 4,823,108 A | 4/1989 | Pope |
| 4,857,893 A | 8/1989 | Carroll |
| 4,868,525 A | 9/1989 | Dias |
| 5,193,056 A | 3/1993 | Boes |
| 5,214,409 A | 5/1993 | Beigel |
| 5,237,669 A | 8/1993 | Spear et al. |
| 5,367,658 A | 11/1994 | Spear et al. |
| 5,430,441 A | 7/1995 | Bickley et al. |

(Continued)

FOREIGN PATENT DOCUMENTS

| | | |
|---|---|---|
| DE | 19535719 A1 | 3/1997 |
| DE | 20106542 U1 | 6/2001 |

(Continued)

OTHER PUBLICATIONS

WO, PCT/US2013/064177 ISR, Mar. 18, 2014.

(Continued)

*Primary Examiner* — Lut Wong
(74) *Attorney, Agent, or Firm* — One LLP

(57) ABSTRACT

A shelf life inference system comprising a container for a plurality of items. The container has coupled to it a tracker operative to read the ID label on each item and to track the exit from and the return to the container of each item separately and to calculate the freshness status of each item upon return to the container.

10 Claims, 5 Drawing Sheets

(56) References Cited

U.S. PATENT DOCUMENTS

| | | |
|---|---|---|
| 5,442,669 A | 8/1995 | Medin |
| 5,491,482 A | 2/1996 | Dingwall et al. |
| 5,519,381 A | 5/1996 | Marsh et al. |
| 5,528,222 A | 6/1996 | Moskowitz et al. |
| 5,563,928 A | 10/1996 | Rostoker et al. |
| 5,564,926 A | 10/1996 | Branemark |
| 5,572,169 A | 11/1996 | Iwamoto |
| 5,640,687 A | 6/1997 | Meron et al. |
| 5,649,295 A | 7/1997 | Shober et al. |
| 5,745,036 A | 4/1998 | Clare |
| 5,798,694 A | 8/1998 | Reber et al. |
| 5,802,015 A | 9/1998 | Rothschild et al. |
| 5,809,518 A | 9/1998 | Lee |
| 5,835,553 A | 11/1998 | Suzuki |
| 5,847,705 A | 12/1998 | Pope |
| 5,850,187 A | 12/1998 | Carrender et al. |
| 5,963,105 A | 10/1999 | Nguyen |
| 5,963,134 A | 10/1999 | Bowers et al. |
| 6,003,115 A | 12/1999 | Spear et al. |
| 6,006,247 A | 12/1999 | Browning et al. |
| 6,012,057 A | 1/2000 | Mayer et al. |
| 6,019,394 A | 2/2000 | Chenoweth et al. |
| 6,023,712 A | 2/2000 | Spear et al. |
| 6,025,780 A | 2/2000 | Bowers et al. |
| 6,094,138 A | 7/2000 | Eberhardt et al. |
| 6,100,804 A | 8/2000 | Brady et al. |
| 6,112,275 A | 8/2000 | Curry et al. |
| 6,116,505 A | 9/2000 | Withrow |
| 6,122,704 A | 9/2000 | Hass et al. |
| 6,147,605 A | 11/2000 | Vega et al. |
| 6,160,458 A | 12/2000 | Cole et al. |
| 6,172,596 B1 | 1/2001 | Cesar et al. |
| 6,185,513 B1 | 2/2001 | Plettner et al. |
| 6,217,213 B1 | 4/2001 | Curry et al. |
| 6,232,870 B1 | 5/2001 | Garber et al. |
| 6,275,779 B1 | 8/2001 | Pohle et al. |
| 6,285,282 B1 | 9/2001 | Dorenbosch et al. |
| 6,294,997 B1 | 9/2001 | Paratore et al. |
| 6,326,892 B1 | 12/2001 | De La Forterie |
| 6,351,406 B1 | 2/2002 | Johnson et al. |
| 6,376,284 B1 | 4/2002 | Gonzalez et al. |
| 6,476,682 B1 | 11/2002 | Cole et al. |
| 6,476,716 B1 | 11/2002 | Ledlow |
| 6,545,938 B2 | 4/2003 | Lee et al. |
| 6,557,760 B2 | 5/2003 | Goodwin, III |
| 6,563,417 B1 | 5/2003 | Shaw |
| 6,593,845 B1 | 7/2003 | Freedman et al. |
| 6,671,358 B1 | 12/2003 | Seidman et al. |
| 6,712,276 B1 | 3/2004 | Abali et al. |
| 6,720,866 B1 | 4/2004 | Sorrells et al. |
| 6,795,376 B2 | 9/2004 | Quine |
| 6,806,698 B2 | 10/2004 | Gauthier et al. |
| 6,826,119 B2 | 11/2004 | Fortune |
| 6,829,520 B1 | 12/2004 | Green |
| 6,857,566 B2 | 2/2005 | Wankmualler |
| 6,860,422 B2 | 3/2005 | Hull et al. |
| 6,863,377 B2 | 3/2005 | Walker et al. |
| 6,927,687 B2 | 8/2005 | Carrender |
| 6,950,028 B2 | 9/2005 | Zweig |
| 6,982,640 B2 | 1/2006 | Lindsay et al. |
| 7,221,270 B2 | 5/2007 | Chen et al. |
| 7,321,774 B1 | 1/2008 | Lau et al. |
| 7,495,558 B2 | 2/2009 | Pope et al. |
| 7,573,370 B2 | 8/2009 | Becker et al. |
| 7,764,183 B2 | 7/2010 | Burchell et al. |
| 7,982,622 B2 | 7/2011 | Burchell et al. |
| 8,068,011 B1 * | 11/2011 | Sajadi ................ H04M 1/7253 340/10.4 |
| 2002/0067265 A1 | 6/2002 | Rudolph |
| 2002/0085453 A1 | 7/2002 | Fortune |
| 2003/0006907 A1 | 1/2003 | Lovegreen et al. |
| 2003/0099157 A1 | 5/2003 | Quine |
| 2004/0000713 A1 | 1/2004 | Yamashita et al. |
| 2004/0008112 A1 | 1/2004 | Carrender |
| 2004/0212509 A1 | 10/2004 | Zweig |
| 2005/0055287 A1 | 3/2005 | Schmidtberg et al. |
| 2005/0108044 A1 | 5/2005 | Koster |
| 2005/0248455 A1 | 11/2005 | Pope et al. |
| 2007/0001862 A1 | 1/2007 | Zweig |
| 2007/0132588 A1 | 6/2007 | Jung et al. |
| 2007/0176773 A1 | 8/2007 | Smolander et al. |
| 2007/0258048 A1 | 11/2007 | Pitchers |
| 2010/0275625 A1 * | 11/2010 | Lowenstein ............ F25D 29/00 62/127 |
| 2011/0098026 A1 | 4/2011 | Uland |

FOREIGN PATENT DOCUMENTS

| | | |
|---|---|---|
| EP | 0837412 A2 | 4/1998 |
| EP | 1319928 A1 | 6/2003 |
| GB | 2259768 A | 3/1993 |

OTHER PUBLICATIONS

EP, 0575639.0 Supplementary Search Report, Dec. 4, 2008.
EP 1384561.2 Supplementary Search Report, Jan. 27, 2016.
WO, PCT/US2005/014047 ISR and Written Opinion, Apr. 23, 2007.
WO, PCT/US2013/064177 IPRP, Sep. 18, 2014.
Grackin, A., "A Midsize Approach to FRID," RFID Journal, Oct. 2004, p. 43.
Jedermann, R., et al., "Shelf-life Prediction by Intelligent RFID Technical Limit of Model Accuracy," International Conference on Dynamics and Logistics, Aug. 28-30, 2007, Bremen Germany, pp. 1-5.
Raynor, M., "RFID and Disruptive Innovation," RFID Journal, Oct. 2004, pp. 27-42.
Roberts, W., et al., "Proposal for Standardized Core Functionality in Digital Time-Temperature Monitoring Devices," White paper by the Temperature Tracking Work Group of the SAL Consortium, Apr. 1, 2001, pp. 1-10.

* cited by examiner

INFERENCE ELECTRONIC SHELF LIFE DATING SYSTEM FOR PERISHABLES

PRIORITY

This application is a continuation application of PCT Patent Application Serial No. PCT/US13/64177, filed Oct. 9, 2013, which claims the benefit of U.S. Provisional Application Ser. No. 61/711,340, filed Oct. 9, 2012, both of which are incorporated herein by reference herein in its entirety.

BACKGROUND

Field of the Invention

The invention relates to systems and methods for inferring the shelf life or the freshness of one or more perishables when the perishables are monitored intermittently throughout their lives or when a perishable is monitored as part of a group of perishables having varying shelf lives. The invention relates to shelf life monitoring sensors and tags, the absence of shelf life monitoring sensors and tags during time periods in a perishable's life, and the perishable packaging, software, systems and processes for monitoring, inferring, estimating and analyzing the shelf life of a perishable product during the time the perishable is away from a monitoring device.

Description of the Related Art

Perishable products, whether produce, meats, fish, pharmaceuticals, blood, chemicals, flowers and other products, each have a unique shelf life. This shelf life is affected by the physical, chemical or biological characteristics of the perishable as well as the packaging of the perishable. Temperature is usually the predominant factor in determining shelf life—with humidity, vibration shock and other factors playing a lesser but important role.

For the last forty years the Use-by or Expiration date printed on a label in words and often supplemented by a barcode has been the predominant label for indicating the end time of a perishable. This date represents the perishable manufacturer's assessment of the temperature and other environmental conditions to be experienced by the perishable from the time it is manufactured until it is used. Because temperature is often different from what was predicted, the date alone is not always an accurate representation of shelf life. If a product is properly transported and stored, it can last much longer than the date. Conversely, if the temperature is higher than predicted, the product deteriorates more quickly in relation to temperature.

Digital shelf life monitoring labels and devices have been developed for the purpose of supplementing or replacing the paper expiration date. In reference to the use of shelf life sensors and labels to determine shelf life, U.S. Pat. Nos. 5,442,669 (Medin), 7,495,558 B2 (Pope), 7,764,183 B2 (Burchell), and 7,982,622 B2 (Burchell) are cited, assigned to Infratab. These patents describe how electronic temperature sensors and labels are used to monitor the shelf life or freshness of a perishable using freshness determining tables in conjunction with temperature sensors to calculate shelf life used and shelf life left of a perishable.

U.S. Pat. No. 5,442,669, Medin, describes a digital shelf life monitor which integrates time and temperature using a freshness determining table based upon spoilage characteristics of a perishable to calculate shelf life used and an LCD gauge for displaying shelf life left. U.S. Pat. No. 7,495,558 B2, Pope et al., adds RFID to the freshness determining table and describes a tag configuration in which sensing is separate from the RFID transponder so as to enable various shapes and sizes of tag and flexibility in support of various RF frequencies. It also adds humidity, vibration and other sensors to both its freshness monitoring and to its freshness determining tables and includes methods of inheriting shelf life from a sensor tag to another sensor tag or an identification tag. U.S. Pat. No. 7,982,622 B2, Burchell et al., adds the use of light and audio to identify items based upon shelf life and describes different physical configurations supported by the two module sensor architecture of the tag.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown.

DETAILED DESCRIPTION OF THE INVENTION

Figure 1:
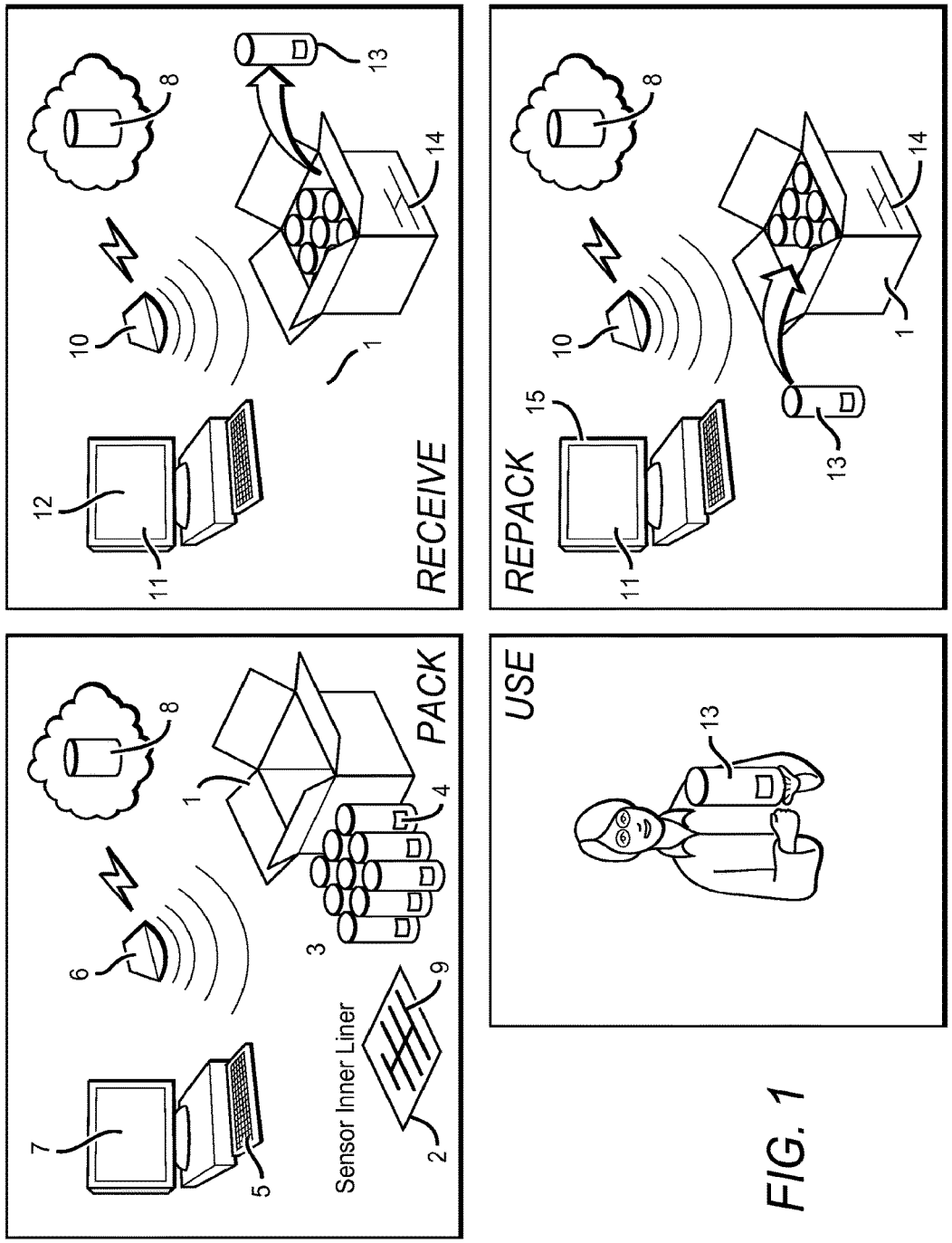
FIG. 1 is a pictorial illustration of a system and methodology for monitoring the shelf life of multiple vaccine vials in a container and for inferring shelf life of the vaccine for the time period a vaccine vial is away from the container. Inference of shelf life while the vaccine is away is calculated by software in an RFID reader.

The invention is based on the realization that a plurality of perishable items could be tracked individually by a single tracker by placing an ID label on each item and retaining the perishables in a container that tracks the exit and time away of item exiting from and returned to the container. The container has coupled to it a tracking device comprising the Freshness trend line data of each perishable and includes software to recalculate freshness of each item responsive to the exit from and return to the container of the item.

This invention addresses the systems and methods for determining the shelf life of a perishable when the cost of a shelf life label is either too expensive to monitor the perishable throughout its entire life, when there are times in the life of the perishable when temperature monitoring is not practical or when the cost of the label is affordable only when multiple perishables, each with different shelf lives, can be monitored as a group and for which the shelf life of the perishable may have to be inferred.

The invention comprises systems and methods for consigning multiple products of a differing nature to a temperature monitored container or space. A temperature controlled container can be as large as a cold storage room, a pre-cooler room, a silo, a reefer, a vat or a refrigerator and as small as a cooler, a vaccine dispensing container or a cosmetics case.

The method for inferring shelf life used when the perishable has been removed from the container is based upon shelf life characteristics of the product as known by the shelf life monitoring tag or device, the temperature when returned and the time duration away. Temperature of the perishable upon return can be measured by the reader or by the tag in the space. The inferred shelf life used while away can be calculated by either the reader or the tag. A confidence factor is calculated by either the tag or the reader, reflecting confidence in the accuracy of the temperature that was read, the assumption that this temperature was the highest temperature that was incurred, and the accuracy of the time duration since the perishable's temperature sensing and shelf life calculation when last in the container.

The system and methodology of inferring shelf life can be used for specific segments of a perishable's life in conjunction with more precise monitoring of temperature and shelf life in other segments of the perishable's life. The confidence factor assigned to an inferred shelf life can increase if during the time out of the container the perishable's temperature is taken. The more times the temperature is taken when away, the greater the confidence in the inferred shelf life.

The system herein includes a remote reading device in close proximity when the container is a refrigerator or display case or at a longer distance when the container is a corn silo, a means of monitoring the temperature of the container and the perishables in the container and away from the container and a means of calculating the shelf life of perishables that are in the container and a means of inferring the shelf life when the perishables are away. Perishables leaving or entering the container are tracked by the reader that is outside of the container. Inferred shelf life used while a perishable is away from a container can be determined in a number of ways, including by the shelf life monitoring tag when the perishable returns or by a reader outside of the container. If a perishable's shelf life metrics and last measurements were recorded into the perishable's RFID identification label when the perishable was removed from the container or were sent to a remote database, inferred shelf life during the time away can be calculated by another reader or device. A reader can be a cell phone or a reader device (RFID, NFC, infrared, magnetic, optical, wireless, Bluetooth, Zigbee). The reader can have its own means of monitoring temperature. The preferred reader for small containers is a cell phone. The preferred reader for larger containers is an RFID ultra-high frequency (UHF) or wireless reader.

The preferred embodiment of the invention consists of a known number of perishables, all placed into the container at the same time, monitored by a multi-sensor shelf life monitoring tag wherein each perishable has its own individual identification label. This label can be a barcode label, and RFID or NFC label, the perishable's marketing label or if a fruit or vegetable the item's price lookup code (PLU). The preferred identification label is a NFC or RFID label. This embodiment provides a base reference for the group of items and enables the shelf life monitoring tags to be set up for the package or container as a unit.

In accordance with this invention a system and methodology are disclosed for tracking a product which departs from a package or base temperature long enough to infer a change in the product's shelf life or to trigger an inference status of the condition of the product. Upon use or return to the container, the perishable's temperature is taken, the time away from the container is verified, an inferred shelf life is estimated, a confidence factor is recorded and if tag history is stored in a remote database, the database is updated.

The method includes the tracking of a known product which is removed from a shelf life monitored container and in which the product's last temperature, its shelf life left and its shelf life metrics are known or can be accessed. In order to infer how much life was used during the time, the perishable was not monitored. The method includes the determination of the time away, the variation in temperature from departure to return, the inference of the change in shelf life that occurred while unmonitored. The inference calculation is further refined by confidence indicator of the temperature experienced while away and by calculations as to whether the current temperature was the highest temperature encountered and by verifications by the perishable handler about the perishable's temperature exposure. The inference calculation of the shelf life used while away can be done by the shelf life monitoring tag in the container or by a reader which can take a temperature reading of the perishable.

Intended embodiments of the invention include a doctor's medicine cabinet or work bag, a home medicine cabinet, a vaccine vial carrying case for sensitive field uses carrying multiple disposable syringes, a smart shelf or bin, a display case for foods at a grocery store, a home refrigerator, a reefer or a silo. When the sensor or monitoring device includes RFID or optical recognition, the perishable can be tracked automatically using a barcode, RFID label or optical recognition of the departing and returning objects.

As part of the shelf life monitoring systems, similar to those described in U.S. Pat. No. 7,495,558 B2, monitored history can be stored in the monitoring device, the reader or sent to a remote database.

The system and method includes smart containers such as smart refrigerators, used in conjunction with remote temperature and item tracking devices, such as an RFID reader or cell phone. In this embodiment, the reading device determines the identity and the temperature of departing and returning objects, tracks the time duration that the objects were in and out of the container and calculates an inferred shelf life used while in the container and while departed.

The invention envisions shelf life determining cases for perishables that include a readable or audible display which can signal an alert when an item in the container is about to or has reached a predefined state, such as "no longer good" or which can be used to check the shelf life when an item departs or returns to the container.

In certain countries, both a closed date for storage, i.e. the manufacturer's Use-by date and an "after when opened" date, might both be assigned to a perishable. The systems and methods envisioned by the invention apply to both or either date.

The invention envisions that within a container there are different temperature controlled compartments. In the example of a silo levels of the silo are considered zones. These zones within the container—either identified to the user in software at the reader or by identifiers within the shelf life monitoring liner for the container.

The invention's primary focus is on highly temperature sensitive products that are out of a monitored environment for short amounts of time (enzymes, reagents), where not having an idea of how much shelf life was used when the object was out of the monitored environment, today, results in the product being tossed rather than used. The inference system envisioned would err on the side of safety, taking into account how long a time the cooled product would take to rise to various temperatures. Included in the inference shelf life is a limit on the total time away from the controlled temperature at the highest temperature envisioned-ensuring that temperature sensitive objects are not used improperly.

The invention further can include additional sensors, for example, humidity, vibration, and pathogens in the system's freshness monitoring component. Wherein the freshness monitoring module receives humidity-dependent, vibration-dependent and other-sensor dependent measurement data, it determines a current freshness status based upon this data and accordingly updates the freshness status.

Embodiments of the invention provide for shelf life monitoring of a plurality of items in a container and for inferring shelf life used when items are removed from the container for a known period of time.

In accordance with the embodiments of the invention, shelf life monitoring tags or devices are either embedded into the container, are configured as removable inner liners designed for the container, or are tags placed inside of the container. The shelf life monitoring tags or devices include a communications transponder module, a sensor module containing one or more sensors for monitoring a plurality of items and environmental conditions, a power module, an optional display module, a software module and a data storage module for storing business data and tag history. The software module includes freshness determining tables for a plurality of items, inference determining modules for pausing monitored shelf life calculations and for inferring shelf life used for items which have been away and have returned to the container.

In the preferred embodiments of the invention individual items in the container are identified by a barcode, RFID tag or NFC identification label. The invention does support items with no serialized identification that are a part of a known and documented batchlot, have an attached printed marketing label or are used in conjunction with a container or inner liner designed for particular shapes and sizes of items, wherein these shapes can be identified as representing a specific item or item group.

In the preferred embodiments readers are configured with (i) shelf life monitoring software or (ii) shelf life inference software or both. Shelf life monitoring software is used to set up the shelf life monitoring tags for the container and group of items in the container, identify items placed into and removed from the container and retrieve temperature and shelf life history from the tag. Shelf life inference software is used to identify an item that is removed from and returns to the container, estimate the shelf life used during a known time duration and assign a confidence factor to the estimate. When the reader has an onboard temperature sensor, the confidence factor becomes higher the more temperature sensings that are taken while the item is away.

Preferred readers are RFID readers used when there are a large number of containers and NFC-enabled cell phones when a limited number of containers or items are being monitored. Other embodiments include wireless LAN, Bluetooth, Zigbee or infrared devices.

The preferred embodiments of the invention draw upon the calculation of shelf life as used in Infratab's shelf life monitoring tags described in U.S. Pat. No. 7,495,558 B2, assigned to Infratab. As described therein, the calculation of shelf life is done based upon freshness determining tables which determine the shelf life used per sensing period. Wherein the preferred data in the tables are determined using Arrhenius kinetics, the tables support shelf life calculations that are linear, exponential or experiential.

The system includes in its preferred embodiment the incorporation of the methodology described in U.S. Pat. No. 7,495,558 B2 for representing shelf life as a percentage of life left and used calculation which defines the life of the perishable as starting at 100 and ending at 0, the use-by end of life of the perishable. The methodology for inferring shelf life used while the perishable is away from the sensor is based upon time duration the perishable has been away from the container, the temperature of the perishable at the time it leaves the container, the temperature at the time it returns to the container and a confidence factor for the inferred shelf life used calculation. The confidence factor takes into consideration time duration since the last sensing, highest temperature perishable was exposed to while away, time and temperature exposure that would cause the perishable to rise to the measured temperature and other factors.

Depending upon the environment of the container and how temperature is measured inside the container, the inferred shelf life used while away can be calculated by the sensing device or by reader or remote software. In accordance with U.S. Pat. No. 7,495,558 B2, shelf life, temperature and time alerts can be set to notify users that the perishable is in trouble. In accordance with U.S. Pat. No. 7,495,558 B2, shelf life status of the perishable can be transferred to daughter sensor, ID tags, barcodes or paper labels if appropriate.

Container—Sensor Configurations

FIG. 1 is a pictorial illustration of a system and method for monitoring the shelf life of multiple vaccine vials 3 stored in a temperature monitored container 1, said container having an inner liner 2 comprising a shelf life monitoring device 9 configured with sensors at specified grid locations within the container. Said purpose of the shelf life monitoring device 9 is to monitor the temperature and determine shelf life used per sensing period for each of the plurality of vaccine vials, for registering vials exiting and entering the container and for inferring shelf life for vaccine vials that have left the container and returned.

In this embodiment each vial has an identity label 4. This identity label can be a barcode, an RFID label or a NFC identity label. In preparation for storing vaccines in the container, a control station, comprising a computer 5, reader 6 and shelf life monitoring software 7, adds the shelf life freshness determining tables of the vaccine into the shelf life monitoring device 9. When vials are placed into container 1, shelf life monitoring software 7 registers the vaccine vials 3 that are placed into the container 1. Data associated with setting up the shelf life monitoring device s and identifying the vials in the container 1 is sent to a remote database 8. When container 1 is received at a location for dispensing vaccines, vaccine vial 13 is removed from container 1. At the receiving location, a control station, comprising a computer 11, reader 10 and shelf life receiving software 12 registers vaccine vial 13 as having left the container 1 and informs the shelf life monitoring device 14. The monitoring device pauses its shelf life calculations for the vial. Shelf life receiving software 12 updates database 8 about the event. When vaccine vial 13 is returned to container 1, shelf life inference software 15 estimates how much shelf life was used when the vial was away, informs the shelf life monitoring device 14 that the vial has returned and sends data about the event to the remote database 8. The shelf life monitoring device updates its history with inferred shelf life calculation and resumes shelf life monitoring for vial 13.

Figure 2:
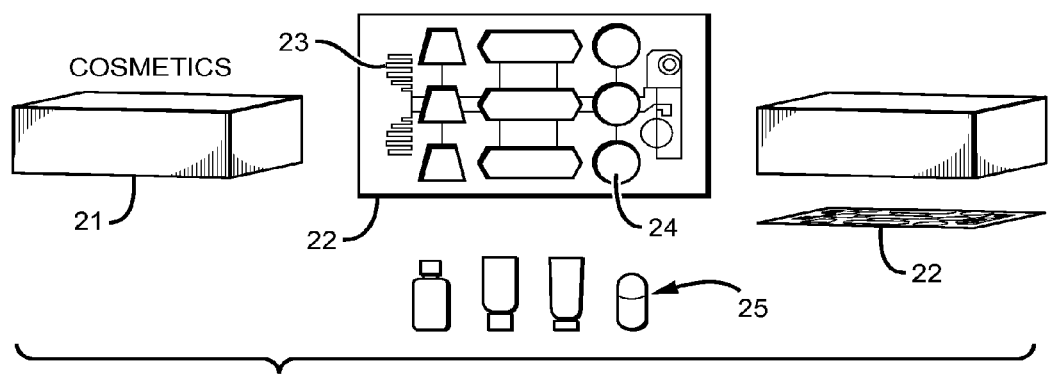
FIG. 2 is a pictorial illustration of a cosmetics case comprising an inner liner designed for cosmetics wherein the identity of the item is correlated to the size and shape of a cutout or marker in the inner liner.

FIG. 2 is a pictorial illustration of a case 21 for monitoring the shelf life of a set of cosmetics bottles or boxes 25, said case 21 comprising a product liner 24 with a cutout or marked grid for various shapes and sizes corresponding to cosmetics bottles and boxes stored in the container and a shelf life monitoring liner 23 comprising a sensor grid corresponding to product liner 24, wherein said purpose of the shelf life monitoring liner 23 is to monitor the temperature and determine shelf life used per sensing period for each of the cosmetics in the container, for registering cosmetics exiting and entering the container and for inferring shelf life for cosmetics 25 that have left the container and returned and wherein the identity of the items are recognized by the size, shape and position of the cutouts or markers of the product inner liner 24.

Figure 3:
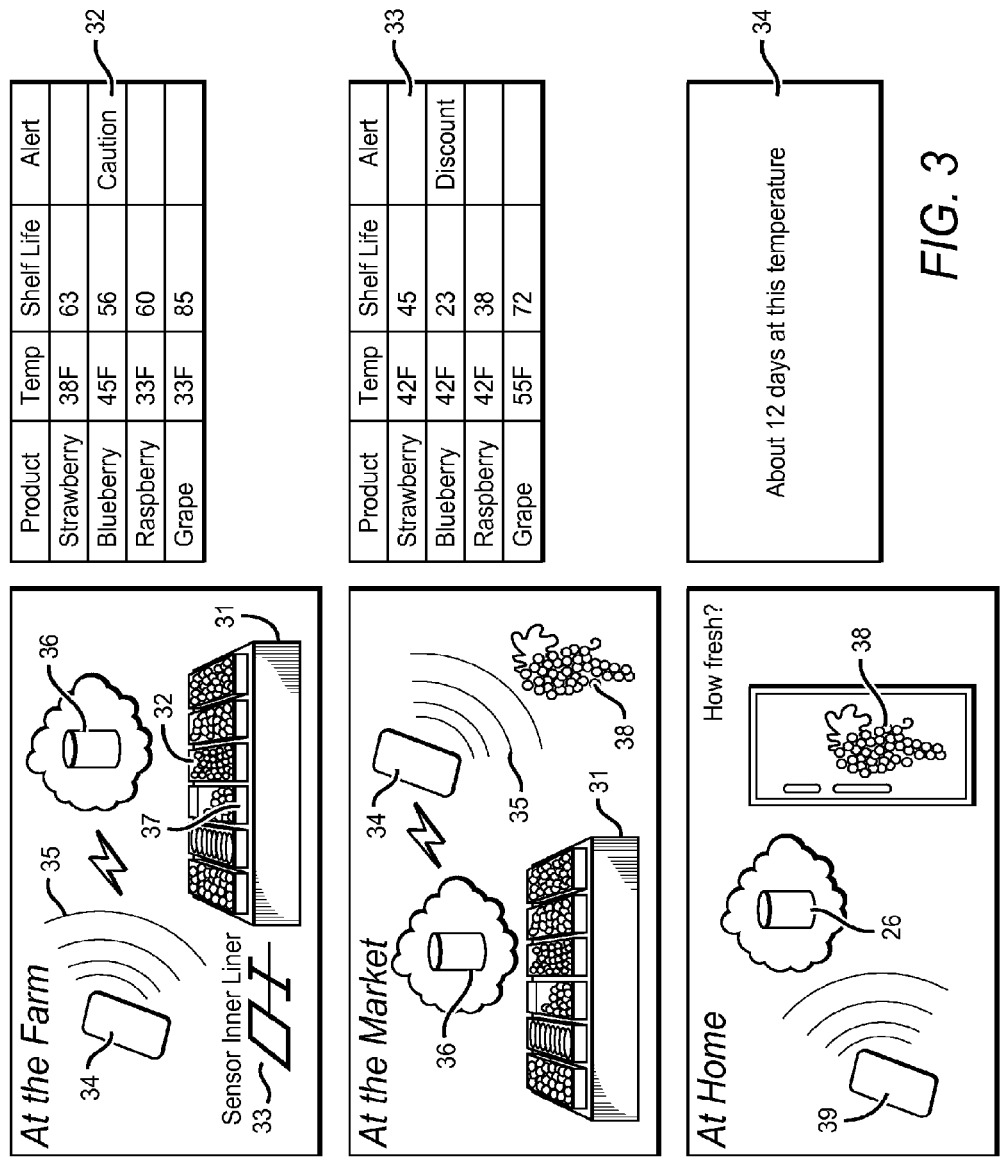
FIG. 3 is a pictorial illustration of a system and methodology for monitoring the shelf life of fruits and vegetable packaged for and sold in a farmers market. Shelf life monitoring for different varieties of vegetables and fruits is done from pack to sale using shelf life monitoring inner liners or long tags placed below the produce and a cell phone running shelf life monitoring and inference software. A software application for a cell phone supports inference calculation by the consumer at the time of consumption.

FIG. 3 is a pictorial illustration of a process for monitoring a container 31 used to store, transport and sell multiple varieties of fruits or vegetables 32 comprising an NFC shelf life monitoring multi-sensor inner liner 33. The use case for this embodiment is a farmer who sells his products at farmers markets. Other use cases include pharmacies, fisheries, hospitals and service providers. Products are tracked by batchlot 37, product variety and location of the farmers market. Shelf life monitoring begins when the items are packed in preparation of the farmers market and ends when all products are sold.

The farmer uses an NFC smartphone 35 with shelf life monitoring software application 34, said application used to communicate to the shelf life monitoring inner liner 33 to set up the device with freshness determining tables for the perishables, to check status, to check out product that is sold and to save tag events in a remote database.

At the market the farmer uses the NFC smartphone 35 with a software application 34 register product sold, get alert conditions 43 of perishables, discount products with life left below a set amount and provide customers with data for use at home with shelf life inference software for consumers. A buyer having a NFC smartphone and consumer inference shelf life software 39 can connect to the remote database 26 and query data about the product purchased 38, for the further use in a home inventory system such as a cupboard or refrigerator. At any time the consumer can measure the temperature of the known item and its packages and update its shelf life for further use by using the software application of the cell phone.

Figure 4:
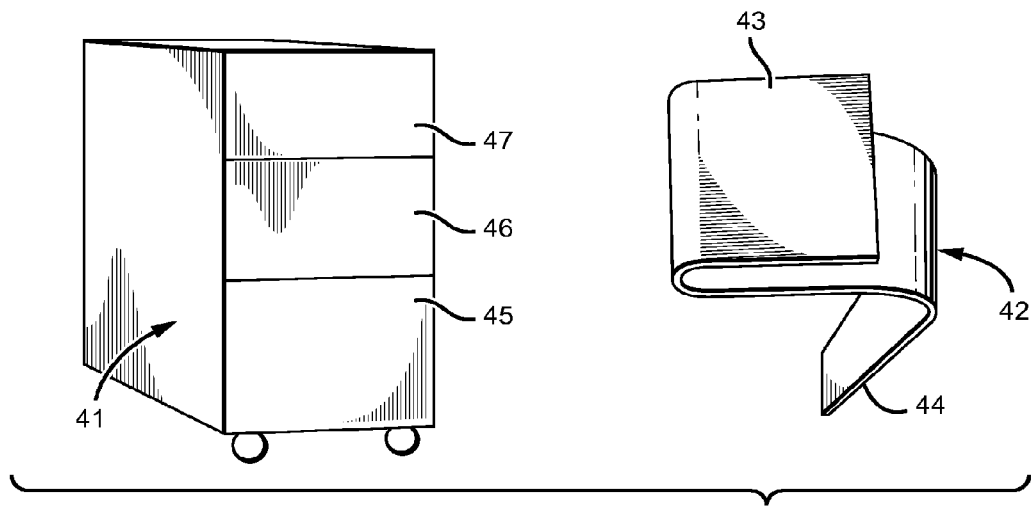
FIG. 4 is a pictorial illustration of a temperature controlled mobile transport container for bio-pharmaceuticals and other temperature sensitive products, wherein shelf life monitoring of the products inside the container is done by zone locations within the container and wherein the shelf life monitoring devices are long tags comprising antenna, power and display modules attached to the outside of the container and sensor modules for monitoring zone locations inside the container.

FIG. 4 is a pictorial illustration of a temperature controlled mobile transport container 41, wherein shelf life monitoring of the products inside the container is done by zone locations within the container 45, 46, 47 and wherein the shelf life monitoring devices are long tags 42 comprising antenna, power and display modules 43 attached to the outside of the container and sensor modules 44 for monitoring zone locations inside the container. Container zone temperatures are monitored, wherein the shelf life determinations for the products in the zone include a confidence factor related to product's location in the zone. In this use case the shelf life and temperature monitoring tags are designed to monitor zones that have previously been determined to have a consistency in the condition being monitored.

This embodiment of the invention is also applicable to non-movable large containers such as silos and vats, where monitoring of certain locations within the container is needed to determine the temperature and shelf life loss rate at various levels of the container.

Figure 5:
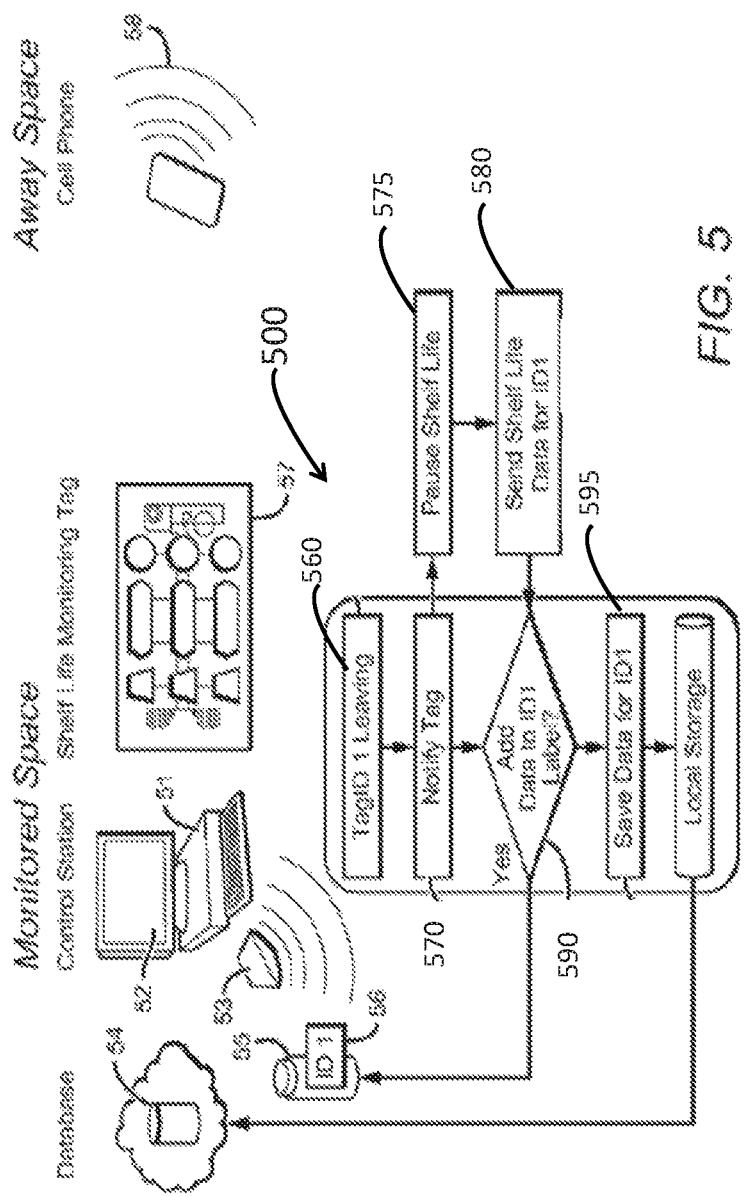
FIG. 5 is a flow chart illustrating a process for inferring shelf life when a product moves away from a temperature or shelf life monitoring device.

FIG. 5 is a flow chart illustrating a process 500 for inferring shelf life when a product moves away from a temperature or shelf life monitoring device. When product 55 with corresponding tag 56 leaves the container (action block 560), shelf life monitoring is stopped in the shelf life monitoring tag 57 until the item returns. The tag 57 is notified by the control station 51 (action block 570), comprised of reader 53 and shelf life monitoring software 52 the item 55 is leaving the container. The tag 57 pauses shelf life monitoring (action block 575) and sends freshness data about the item, comprised of shelf life left, current temperature of the item, last sample time and summary of shelf life spoilage characteristics of the item (action block 580). If the item has an RFID or NFC ID label 56 attached to the item (decision block 590), the shelf life monitoring software 52 will write the shelf life summary data supplied by the tag 57 to the ID label 56. The shelf life monitoring software 52 will also store the data (action block 595) and will send the information that the item is leaving and the shelf life summary data for the item to a remote database 54.

Figure 6:
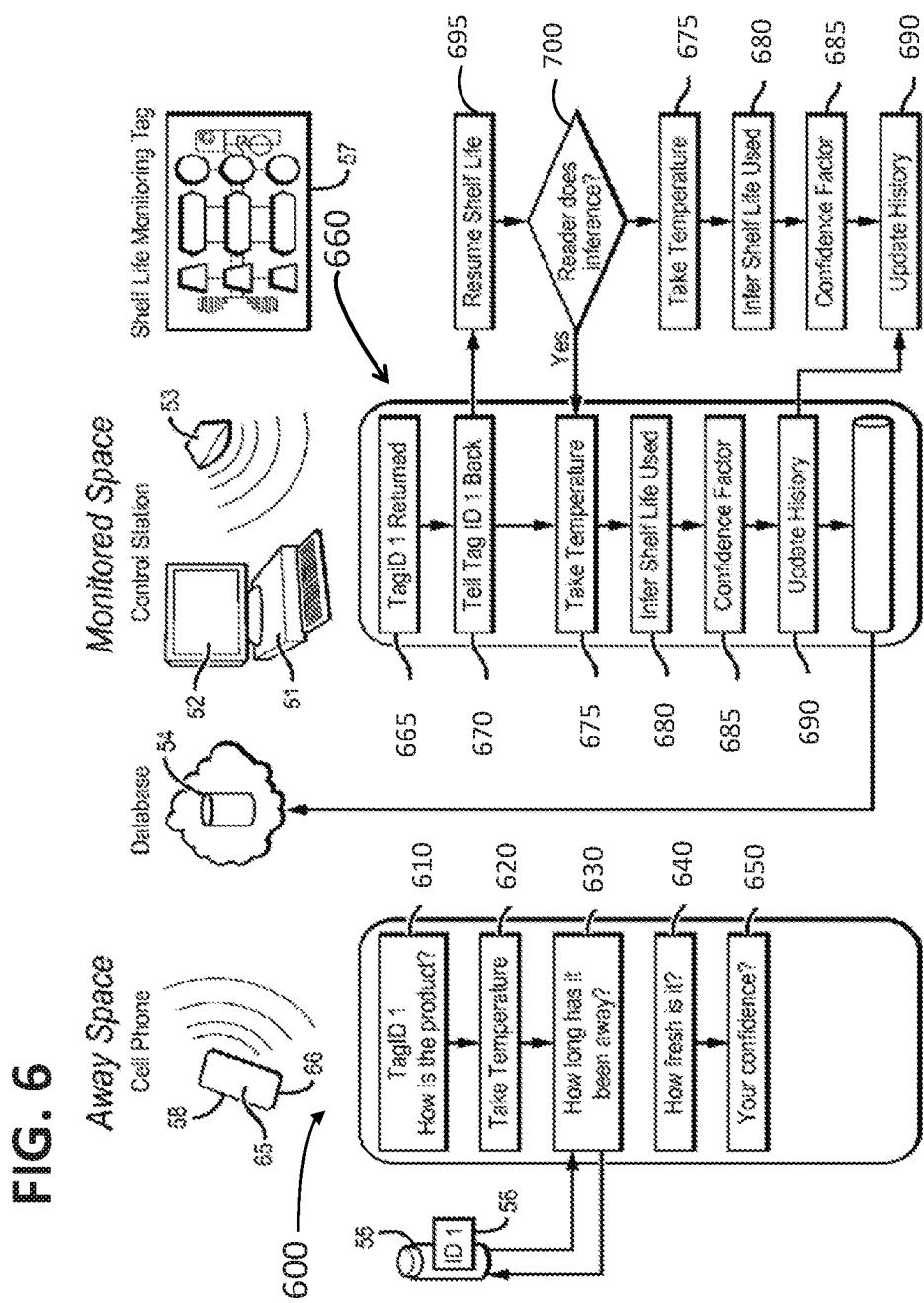
FIG. 6 is another flow chart illustrating a process for inferring shelf life when a product returns to a temperature of shelf life monitoring device.

Turning to FIG. 6, a flow chart illustrating a process 600 for inferring shelf life when the product is away from monitoring tag 57. When the tagged item 55 is away, a perishable handler of the item can infer how much shelf life has been used and how much shelf life is left for the tagged item 55. To do this the perishable handler has to have a device 58 that can read the ID label 56 of the item 55 (action block 610). The preferred reader is an NFC smart phone capable of running a shelf life inference software application 65. The perishable handler has to also have a means of taking the temperature of the perishable item 55. The preferred system for taking the temperature is an add-on module to a cellphone which senses temperature of items in the proximity of the cellphone 66. The shelf life inference software 65 takes the current temperature and time (action blocks 620 and 630). Using the cell phone's NFC communications 66, the shelf life inference software accesses the data in the ID tag 56, calculates how much freshness has been used since the last temperature sensing, and asks the user about highest temperature the item has encountered in the time away (action block 640). The more frequently that temperature of the perishable item is taken, the higher the confidence factor (action block 650).

A process 660 executed when the perishable item 55 is returned to its container is shown. When the perishable item 55 is returned to its container (action block 665), the shelf life inference software 52 running in control station 51 will notify the shelf life monitoring tag 57 via the reader 53 that the perishable item has returned (action block 670). The tag 57 will resume its shelf life monitoring of the item (action block 695). The inference software 52 will also determine if it or tag 57 will make the calculation as to shelf life used while the item 55 was away (decision block 700). Either the tag 57 or the inference software 52 can do this. When shelf life used and shelf life left for the perishable item is calculated (action block 680), both the tag 57 and the inference software will update their history (action block 690). The inference software running in the control station will also send data about the event to the remote database.

What is claimed is:

1. A system for tracking the shelf life status of one or more perishables removed from and/or returned to a container, containing a plurality of perishables, said system comprising:
   an ID label associated with each of said plurality of perishables;
   one or more sensors in the container operative at periodic sensing periods to sense the temperature of each of said plurality of perishables in a container;
   a tracking device, communicatively coupled to said container operative to calculate and/or record at each periodic sensing the shelf life status of said plurality of perishables in the container using the sensed temperature and responsive to the movement of a perishable exiting said container to calculate and/or record the exit shelf life status for the associated perishable based upon the exit temperature of the perishable, the elapsed time since last sensing and spoilage characteristics of said perishable;
   said perishable being moved to a position where there is no temperature monitoring;
   said tracking device being operative to sense the temperature of said perishable entering a container, calculate the shelf life, using the temperature sensed and the spoilage characteristics of the perishable for the time that the perishable was not temperature monitored, and subtract an away freshness shelf life status, which is defined by the time the perishable was not temperature monitored, from said exiting shelf life status, wherein the difference identifies the amount of remaining shelf life if greater than zero.

2. A system as in claim 1 wherein said tracking device is attached to said container.

3. A system as in claim 1 wherein tracking device is remote from said container.

4. A system as in claim 1 wherein said container comprises one or more sensor liners and comprises a tracking device coupled to each of said liners.

5. A system as in claim 4 comprising wherein the tracking device coupled to each of said liners comprises shelf life trends for each of the items in the associated liner.

6. A system as in claim 1 wherein said tracking device comprises software for determining time out of the container of an item, the temperature at exit and the temperature at entrance of the item.

7. A system as in claim 1 wherein said tracking device comprises a cell phone and a tracker being operative to calculate or record shelf life status for each of said items and/or updating said data responsive to the exit from and/or entrance to said container or ID label.

8. A system as in claim 1, wherein said container has an access door.

9. A system as in claim 1, wherein an ID label is attached to each of said perishables.

10. A method for tracking the shelf life status of one or more perishables removed from and/or returned to a container containing a plurality of perishables comprising:
    attaching an ID label to each of said plurality of perishables;
    placing the one or more perishables in a container, said container having one or more sensors in the container operative at periodic sensing periods to sense the temperature of each of said plurality of perishables in the container;
    communicatively coupling to the container a tracking device operative to calculate and/or record at each periodic sensing the shelf life status of said plurality of perishables in the container using the sensed temperature, the elapsed time since last sensing and spoilage characteristics of each of said perishables and responsive to the exiting of a perishable for calculating and/or recording an exit shelf life status based upon the exit temperature of the perishable, elapsed time since the last temperature sensing and the spoilage characteristics of the perishable item;
    moving said perishable to a position where there is no temperature monitoring; and
    returning a perishable to a container with a tracking device operative to sense the temperature of said perishable entering the container, calculate the shelf life, using the sensed temperature and the spoilage characteristics for the time the perishable was not temperature monitored and subtract an away shelf life status, which is defined by the time the perishable was not temperature monitored, from said exit shelf life status, wherein the difference identifies the amount of remaining freshness if greater than zero.

* * * * *